(12) United States Patent
Nelson et al.

(10) Patent No.: US 11,795,345 B2
(45) Date of Patent: *Oct. 24, 2023

(54) PROCESSES FOR PRODUCING LIGNIN-COATED HYDROPHOBIC CELLULOSE, AND COMPOSITIONS AND PRODUCTS PRODUCED THEREFROM

(71) Applicant: GranBio Intellectual Property Holdings, LLC, Minnetrista, MN (US)

(72) Inventors: Kimberly Nelson, Atlanta, GA (US); Theodora Retsina, Atlanta, GA (US); Vesa Pylkkanen, Atlanta, GA (US); Ryan O'Connor, Minnetrista, MN (US)

(73) Assignee: GranBio Intellectual Property Holdings, LLC, Thomaston, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/498,014

(22) Filed: Oct. 11, 2021

(65) Prior Publication Data

US 2022/0098440 A1 Mar. 31, 2022

Related U.S. Application Data

(63) Continuation of application No. 16/663,671, filed on Oct. 25, 2019, now Pat. No. 11,142,668, which is a continuation of application No. 15/609,836, filed on May 31, 2017, now abandoned, which is a continuation of application No. 14/606,200, filed on Jan. 27, 2015, now abandoned.

(60) Provisional application No. 61/980,996, filed on Apr. 17, 2014, provisional application No. 61/941,241, filed on Feb. 18, 2014.

(51) Int. Cl.

| | | |
|---|---|---|
| C09D 197/00 | (2006.01) |
| C12P 19/02 | (2006.01) |
| C04B 16/02 | (2006.01) |
| C12P 19/14 | (2006.01) |
| C09K 8/035 | (2006.01) |
| C08B 37/00 | (2006.01) |
| C08H 7/00 | (2011.01) |
| C08H 8/00 | (2010.01) |
| C08L 1/02 | (2006.01) |
| C08L 5/14 | (2006.01) |
| C08L 97/00 | (2006.01) |
| C08L 97/02 | (2006.01) |
| C12P 7/10 | (2006.01) |
| C13K 1/02 | (2006.01) |
| D21H 17/23 | (2006.01) |
| D21H 17/25 | (2006.01) |
| D21H 19/34 | (2006.01) |
| D21H 19/52 | (2006.01) |

(52) U.S. Cl.
CPC .......... *C09D 197/005* (2013.01); *C04B 16/02* (2013.01); *C08B 37/0057* (2013.01); *C08H 6/00* (2013.01); *C08H 8/00* (2013.01); *C08L 1/02* (2013.01); *C08L 5/14* (2013.01); *C08L 97/005* (2013.01); *C08L 97/02* (2013.01); *C09K 8/035* (2013.01); *C12P 7/10* (2013.01); *C12P 19/02* (2013.01); *C12P 19/14* (2013.01); *C13K 1/02* (2013.01); *C09K 2208/08* (2013.01); *C12P 2203/00* (2013.01); *D21H 17/23* (2013.01); *D21H 17/25* (2013.01); *D21H 19/34* (2013.01); *D21H 19/52* (2013.01); *Y02E 50/10* (2013.01); *Y10T 428/2991* (2015.01)

(58) Field of Classification Search
CPC ........ C09D 197/005; C12P 7/10; C12P 19/02; C12P 2203/00; C04B 16/02; C04B 37/0057; C08H 6/00; C08H 8/00; C08L 1/02; C08L 5/14; C08L 97/005; C08L 97/02; C09K 8/035; C09K 2208/08; C13K 1/02; Y10T 428/2991; D21H 17/23; D21H 17/25; D21H 19/34; D21H 19/52; Y02E 50/10
USPC .......................................................... 435/99
See application file for complete search history.

(56) References Cited

U.S. PATENT DOCUMENTS

| | | | | |
|---|---|---|---|---|
| 5,846,787 A | * | 12/1998 | Ladisch | ......... C12Y 302/01004 |
| | | | | 435/99 |
| 2011/0003352 A1 | * | 1/2011 | Retsina | ..................... C08B 3/00 |
| | | | | 435/157 |
| 2013/0244290 A1 | * | 9/2013 | Retsina | ..................... C12P 7/06 |
| | | | | 435/165 |

\* cited by examiner

*Primary Examiner* — Jennifer M. H. Tichy
(74) *Attorney, Agent, or Firm* — O'Connor & Company; Ryan P. O'Connor

(57) ABSTRACT

Processes disclosed are capable of converting biomass into high-crystallinity, hydrophobic cellulose. In some variations, the process includes fractionating biomass with an acid (such as sulfur dioxide), a solvent (such as ethanol), and water, to generate cellulose-rich solids and a liquid containing hemicellulose and lignin; and depositing lignin onto cellulose fibers to produce lignin-coated cellulose materials (such as dissolving pulp). The crystallinity of the cellulose material may be 80% or higher, translating into good reinforcing properties for composites. Optionally, sugars derived from amorphous cellulose and hemicellulose may be separately fermented, such as to monomers for various polymers. These polymers may be combined with the hydrophobic cellulose to form completely renewable composites.

15 Claims, 4 Drawing Sheets

PROCESSES FOR PRODUCING LIGNIN-COATED HYDROPHOBIC CELLULOSE, AND COMPOSITIONS AND PRODUCTS PRODUCED THEREFROM

PRIORITY DATA

This patent application is a continuation application of U.S. Pat. No. 11,142,668, issued on Oct. 12, 2021, which is a continuation application of U.S. patent application Ser. No. 15/609,836, filed on May 31, 2017, which is a continuation application of U.S. patent application Ser. No. 14/606,200, filed on Jan. 27, 2015, which claims priority to U.S. Provisional Patent App. No. 61/941,241, filed on Feb. 18, 2014 and to U.S. Provisional Patent App. No. 61/980,996, filed on Apr. 17, 2014, each of which is hereby incorporated by reference herein.

FIELD

The present invention generally relates to cellulose and related materials produced by fractionating lignocellulosic biomass and further processing the cellulose fraction.

BACKGROUND

Biomass refining (or biorefining) has become more prevalent in industry. Cellulose fibers and sugars, hemicellulose sugars, lignin, syngas, and derivatives of these intermediates are being utilized for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Cellulose or cellulose derivatives can be used in a wide variety of applications such as polymer reinforcement, antimicrobial films, biodegradable food packaging, printing papers, pigments and inks, paper and board packaging, barrier films, adhesives, biocomposites, wound healing, pharmaceuticals and drug delivery, textiles, water-soluble polymers, construction materials, recyclable interior and structural components for the transportation industry, rheology modifiers, low-calorie food additives, cosmetics thickeners, pharmaceutical tablet binders, bioactive paper, pickering stabilizers for emulsion and particle stabilized foams, paint formulations, films for optical switching, and detergents.

For some cellulose applications, it would be beneficial to increase the hydrophobicity of the cellulose. Therefore, improved processes are needed in the art.

SUMMARY

In some variations, the present invention provides a process for producing a lignin-coated cellulose material, the process comprising:

(a) providing a lignocellulosic biomass feedstock;
(b) fractionating the feedstock in the presence of an acid, a solvent for lignin, and water, to generate cellulose-rich solids and a liquid containing hemicellulose and lignin;
(c) depositing at least some of the lignin, from the liquid, onto a surface of the cellulose-rich solids to generate a lignin-coated cellulose material;
(d) optionally mechanically treating the lignin-coated cellulose material; and
(e) recovering the lignin-coated cellulose material, wherein the cellulose crystallinity of the lignin-coated cellulose material is at least 60%, and wherein the lignin-coated cellulose material is at least partially hydrophobic.

In some embodiments, the acid is selected from the group consisting of sulfur dioxide, sulfurous acid, sulfur trioxide, sulfuric acid, lignosulfonic acid, and combinations thereof. In certain embodiments, the acid is sulfur dioxide. In step (b), exemplary conditions include $SO_2$ concentration from about 12 wt % to about 30 wt %, fractionation temperature from about 140° C. to about 170° C., and fractionation time is from about 1 hour to about 2 hours.

Step (c) is performed either in the same unit as step (b), such as a digestor, or in another unit. Step (c) may occur sequentially following step (b), or simultaneously with step (b), or some combination thereof. Conditions may be selected or optimized to promote deposition of lignin onto the cellulose. For example, longer time, higher temperature, lower pH, and/or lower concentration of the solvent for lignin may be utilized to cause or promote lignin deposition during step (c). In some embodiments, conditions of step (c) are different than those of step (b), and physically separate units are employed (or employed in one unit in a batch-wise process). In other embodiments, a single set of conditions for steps (b) and (c) are selected, and steps (b) and (c) are combined into a single reactor.

When step (d) is performed, steps (c) and (d) may be integrated so that some lignin is physically deposited onto cellulose during mechanical treatment. In some embodiments, the lignin-coated cellulose material is treated with a total mechanical energy of less than about 1000 kilowatt-hours per ton of the lignin-coated cellulose material, such as less than about 500 kilowatt-hours per ton of the lignin-coated cellulose material. In certain embodiments, the total mechanical energy is from about 100 kilowatt-hours to about 400 kilowatt-hours per ton of the lignin-coated cellulose material.

The process may further include treatment of the lignin-coated cellulose material with one or more enzymes or with one or more acids. Such acids may be selected from the group consisting of sulfur dioxide, sulfurous acid, lignosulfonic acid, acetic acid, formic acid, and combinations thereof. Alternatively or additionally, the process may further include treatment of the lignin-coated cellulose material with heat.

In some embodiments, the cellulose crystallinity of the lignin-coated cellulose material is at least 70%, such as at least 80% or 85%.

The lignin-coated cellulose material may include or consist essentially of lignin-coated dissolving pulp, lignin-coated fibrillated cellulose, lignin-coated microcrystalline cellulose, lignin-coated nanocellulose, or other forms of lignin-coated pulp.

The lignin-coated cellulose material may be characterized by an average degree of polymerization from about 100 to about 1500, such as from about 300 to about 700 or from about 150 to about 250.

Optionally, the process further comprises hydrolyzing amorphous cellulose, contained in the lignocellulosic biomass feedstock, into glucose, and optionally fermenting the glucose to a fermentation product. Also optionally, the process further comprises recovering, fermenting, or further treating hemicellulosic sugars derived from the hemicellulose.

In certain embodiments, the process comprises fermenting the hemicellulosic sugars to produce a monomer or precursor thereof; polymerizing the monomer to produce a polymer; and combining the polymer and the lignin-coated cellulose material to form a polymer-cellulose composite.

In some embodiments, the process further comprises recovering, combusting, or further treating the lignin that does not deposit onto the cellulose-rich solids during step (c). The process may further comprise chemically converting the lignin-coated cellulose material to one or more lignin-coated cellulose derivatives such as cellulose esters, cellulose ethers, cellulose ether esters, alkylated cellulose compounds, cross-linked cellulose compounds, acid-functionalized cellulose compounds, base-functionalized cellulose compounds, or combinations thereof.

Some variations provide a process for producing a hydrophobic cellulose material, the process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, wherein a portion of the lignin deposits onto a surface of the cellulose-rich solids, thereby rendering the cellulose-rich solids at least partially hydrophobic;
(c) optionally mechanically treating the cellulose-rich solids to form cellulose fibrils and/or cellulose crystals, having a crystallinity of at least 60%; and
(d) recovering the hydrophobic cellulose material.

In some embodiments, the acid is selected from the group consisting of sulfur dioxide, sulfurous acid, sulfur trioxide, sulfuric acid, lignosulfonic acid, and combinations thereof.

The crystallinity of the hydrophobic cellulose material may at least 70% or at least 80%. The hydrophobic cellulose material may be characterized by an average degree of polymerization from about 100 to about 1500, such as about 300 to about 700 or about 150 to about 250.

Optionally, the process further comprises chemically modifying the lignin to increase hydrophobicity of the hydrophobic cellulose material. Such modification to lignin could be done in solution or after the lignin is deposited onto cellulose.

Variations provide a process for producing a cellulose-containing product, the process comprising providing a lignin-coated cellulose material or a hydrophobic cellulose material, and then incorporating at least a portion of the lignin-coated cellulose material or the hydrophobic cellulose material into a cellulose-containing product.

In some embodiments, the process comprises forming a structural object that includes the cellulose material, or a derivative thereof. In certain embodiments, the process comprises forming a foam or aerogel that includes the cellulose material, or a derivative thereof.

In some embodiments, the process comprises combining the cellulose material, or a derivative thereof, with one or more other materials to form a composite. The one or more other materials may include a polymer selected from polyolefins, polyesters, polyurethanes, polyamides, or combinations thereof. The one or more other materials may include carbon.

In some embodiments, the process comprises forming a film (such as a flexible film) comprising the cellulose material, or a derivative thereof. In some embodiments, the process comprises forming a coating or coating precursor comprising the cellulose material, or a derivative thereof.

In some embodiments, the cellulose-containing product is configured electrochemically for carrying or storing an electrical current or voltage.

In some embodiments, the cellulose-containing product is incorporated into a filter, membrane, or other separation device.

In some embodiments, the cellulose-containing product is incorporated as an additive into a coating, paint, or adhesive.

In some embodiments, the cellulose-containing product is configured as a catalyst, catalyst substrate, or co-catalyst.

In some embodiments, the cellulose-containing product is incorporated as a cement additive.

In some embodiments, the cellulose-containing product is a paper coating.

In some embodiments, the cellulose-containing product is a moisture-barrier pressed pulp product.

In some embodiments, the cellulose-containing product is incorporated as a thickening agent or rheological modifier.

In some embodiments, the cellulose-containing product is incorporated as an additive in a drilling fluid, such as an oil recovery fluid and/or a gas recovery fluid.

A hydrophobic cellulose composition is disclosed with a cellulose crystallinity of about 70% or greater, wherein the hydrophobic cellulose composition contains cellulose particles having a surface concentration of lignin that is greater than a bulk concentration of lignin.

In some embodiments, the cellulose crystallinity is about 75% or greater, such as about 80% or 80% or greater.

In some embodiments, the hydrophobic cellulose composition further comprises sulfur. The sulfur may be derived from the process to produce the hydrophobic cellulose, or otherwise incorporated into the composition.

In some embodiments, the hydrophobic cellulose composition is characterized by an average cellulose degree of polymerization from about 100 to about 1500, such as about 300 to about 700 or about 150 to about 250. The composition may be characterized by a cellulose degree of polymerization distribution having a single peak or two peaks, for example.

In various embodiments, the cellulose-containing product is selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a moisture-barrier pressed pulp product, a thickening agent, a rheological modifier, an additive for a drilling fluid, and combinations or derivatives thereof.

DETAILED DESCRIPTION OF SOME EMBODIMENTS

Figure 1:
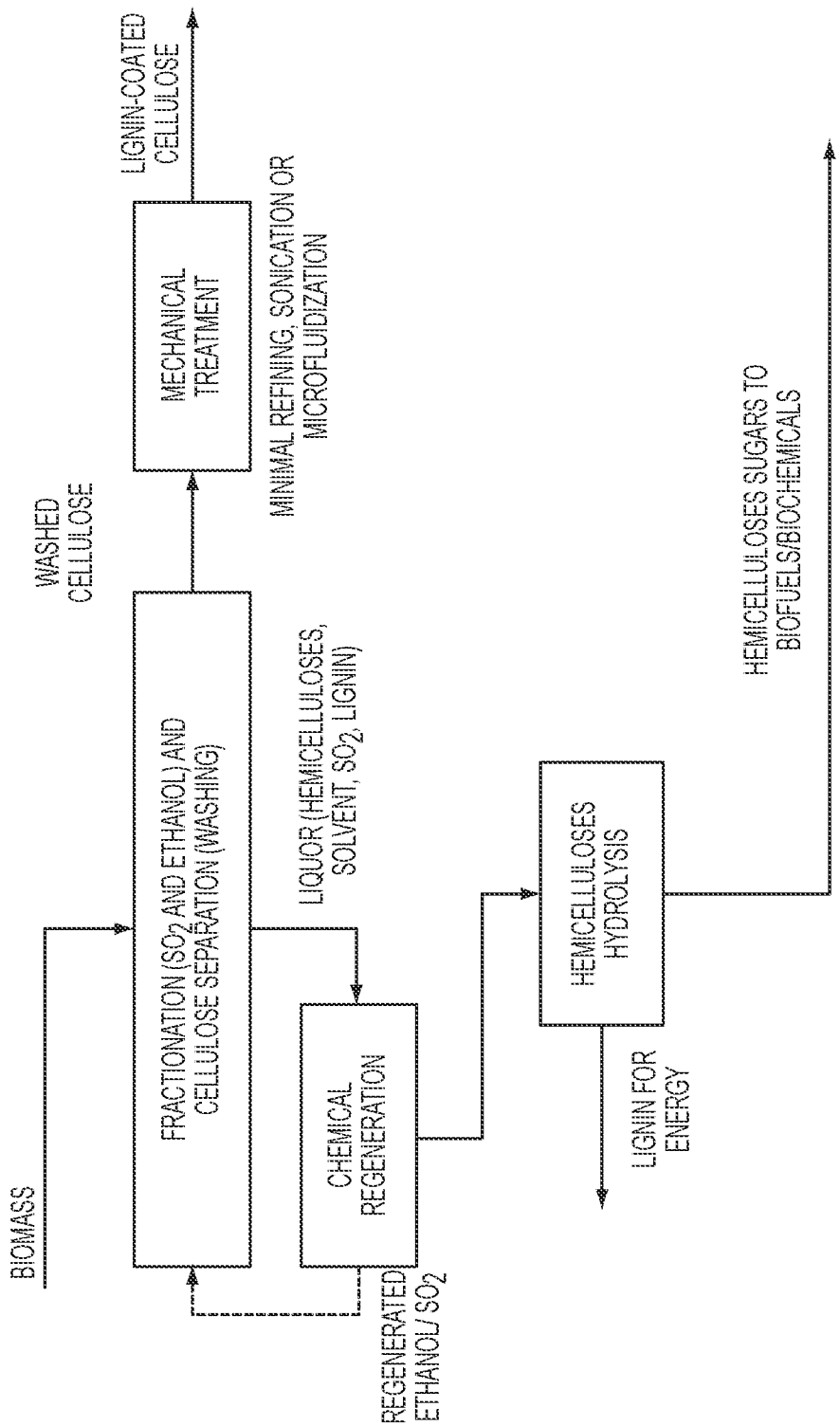
FIG. 1 depicts the production of lignin-coated cellulose materials from biomass, according to some embodiments of the invention. Mechanical treatment is optional.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Generally it is beneficial to process biomass in a way that effectively separates the major fractions (cellulose, hemicellulose, and lignin) from each other. Fractionation of lignocellulosics leads to release of cellulosic fibers and opens the cell wall structure by dissolution of lignin and hemicellulose between the cellulose microfibrils. The fibers become more accessible for conversion to fibrils or crystals. Hemicellulose sugars can be fermented to a variety of products, such as ethanol, or converted to other chemicals. Lignin from biomass has value as a solid fuel and also as an energy feedstock to produce liquid fuels, synthesis gas, or hydrogen; and as an intermediate to make a variety of polymeric compounds. Additionally, minor components such as proteins or rare sugars can be extracted and purified for specialty applications.

This disclosure describes processes and apparatus to efficiently fractionate any lignocellulosic-based biomass into its primary major components (cellulose, lignin, and if present, hemicellulose) so that each can be used in potentially distinct processes. An advantage of the process is that it produces cellulose-rich solids while concurrently producing a liquid phase containing a high yield of both hemicellulose sugars and lignin, and low quantities of lignin and hemicellulose degradation products. The flexible fractionation technique enables multiple uses for the products. The cellulose is an advantaged precursor for producing lignin-coated cellulose, as will be described herein.

The present invention, in some variations, is premised on the discovery that lignin-coated cellulose and related materials can be produced under certain conditions including process conditions and steps associated with the AVAP® process. It has been found, surprisingly, that very high crystallinity can be produced and maintained, without the need for an enzymatic or separate acid treatment step to hydrolyze amorphous cellulose. High crystallinity can translate to mechanically strong fibers or good physical reinforcing properties, which are advantageous for composites, reinforced polymers, and high-strength spun fibers and textiles, for example.

Using sulfur dioxide ($SO_2$) and ethanol (or other solvent), the pretreatment disclosed herein effectively removes not only hemicelluloses and lignin from biomass but also the amorphous regions of cellulose, giving a unique, highly crystalline cellulose material that requires minimal mechanical energy for reduction of fiber size. The low mechanical energy requirement results from the fibrillated cellulose network formed during chemical pretreatment upon removal of the amorphous regions of cellulose.

As intended herein, cellulose products may include a range of cellulosic materials, including but not limited to market pulp, dissolving pulp, particulated cellulose, fibrillated cellulose, microfibrillated cellulose, nanofibrillated cellulose, microcrystalline cellulose, and nanocrystalline cellulose.

"Nanofibrillated cellulose" or equivalently "cellulose nanofibrils" means cellulose fibers or regions that contain nanometer-sized particles or fibers, or both micron-sized and nanometer-sized particles or fibers. "Nanocrystalline cellulose" or equivalently "cellulose nanocrystals" means cellulose particles, regions, or crystals that contain nanometer-sized domains, or both micron-sized and nanometer-sized domains. "Micron-sized" includes from 1 to 100 μm and "nanometer-sized" includes from 0.01 nm to 1000 nm (1 μm). Larger domains (including long fibers) may also be present in these materials.

As used herein, "lignin-coated cellulose" means cellulose particles or fibers which contain lignin on or near the surface of the particles or fibers. Lignin may also be present in the bulk (internal) portion of the cellulose particles or fibers, but the concentration of lignin at the surface is higher than the concentration of lignin in the internal portion. Lignin-coated cellulose may be produced according to the processes disclosed herein, comprising depositing lignin that has been first solubilized by delignification and then undergoes precipitation onto the cellulose. There may be some chemical changes that take place upon lignin precipitation (e.g., condensation chemistry) to alter hydrophobicity, molecular weight, sulfur content, oxygen content, —OH group content, and so on. The surface coating is not necessarily continuous or uniform in chemical composition, hydrophobicity, or thickness.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for purposes of illustrating some embodiments only.

In some variations, the present invention provides a process for producing a lignin-coated cellulose material, the process comprising:

(a) providing a lignocellulosic biomass feedstock;

(b) fractionating the feedstock in the presence of an acid, a solvent for lignin, and water, to generate cellulose-rich solids and a liquid containing hemicellulose and lignin;

(c) depositing at least some of the lignin, from the liquid, onto a surface of the cellulose-rich solids to generate a lignin-coated cellulose material;

(d) optionally mechanically treating the lignin-coated cellulose material; and (e) recovering the lignin-coated cellulose material, wherein the lignin-coated cellulose material is at least partially hydrophobic.

In some embodiments, the acid is selected from the group consisting of sulfur dioxide, sulfurous acid, sulfur trioxide, sulfuric acid, lignosulfonic acid, and combinations thereof. In certain embodiments, the acid is sulfur dioxide. In step (b), exemplary conditions include $SO_2$ concentration from about 12 wt % to about 30 wt %, fractionation temperature from about 140° C. to about 170° C., and fractionation time is from about 1 hour to about 2 hours.

Step (c) is performed either in the same unit as step (b), such as a digestor, or in another unit. Step (c) may occur sequentially following step (b), or simultaneously with step (b), or some combination thereof. Conditions may be selected or optimized to promote deposition of lignin onto the cellulose. For example, longer time, higher temperature, lower pH, and/or lower concentration of the solvent for lignin may be utilized to cause or promote lignin deposition during step (c). In some embodiments, conditions of step (c) are different than those of step (b), and physically separate units are employed (or employed in one unit in a batch-wise process). In other embodiments, a single set of conditions for steps (b) and (c) are selected, and steps (b) and (c) are combined into a single reactor.

Conditions to promote deposition of lignin onto the cellulose may be selected according to the Examples and other disclosure in U.S. Patent App. No. 61/941,215, which is commonly assigned and which has been filed of even date herewith (Feb. 18, 2014). U.S. Patent App. No. 61/941,215 is hereby incorporated by reference herein in its entirety.

When step (d) is performed, steps (c) and (d) may be integrated so that some lignin is physically deposited onto cellulose during mechanical treatment. In some embodiments, the lignin-coated cellulose material is treated with a total mechanical energy of less than about 1000 kilowatt-hours per ton of the lignin-coated cellulose material, such as less than about 500 kilowatt-hours per ton of the lignin-coated cellulose material. In certain embodiments, the total mechanical energy is from about 100 kilowatt-hours to about 400 kilowatt-hours per ton of the lignin-coated cellulose material.

The process may further include treatment of the lignin-coated cellulose material with one or more enzymes or with one or more acids. Such acids may be selected from the group consisting of sulfur dioxide, sulfurous acid, lignosulfonic acid, acetic acid, formic acid, and combinations thereof. Alternatively or additionally, the process may further include treatment of the lignin-coated cellulose material with heat.

In some embodiments, the crystallinity of the lignin-coated cellulose material is at least 70%, such as at least 80% or 85%.

The lignin-coated cellulose material may include or consist essentially of lignin-coated dissolving pulp, lignin-coated fibrillated cellulose, lignin-coated microcrystalline cellulose, lignin-coated nanocellulose, or other forms of lignin-coated pulp.

The lignin-coated cellulose material may be characterized by an average degree of polymerization from about 100 to about 1500, such as from about 300 to about 700 or from about 150 to about 250.

Optionally, the process further comprises hydrolyzing amorphous cellulose, contained in the lignocellulosic biomass feedstock, into glucose, and optionally fermenting the glucose to a fermentation product. Also optionally, the process further comprises recovering, fermenting, or further treating hemicellulosic sugars derived from the hemicellulose.

In certain embodiments, the process comprises fermenting the hemicellulosic sugars to produce a monomer or precursor thereof; polymerizing the monomer to produce a polymer; and combining the polymer and the lignin-coated cellulose material to form a polymer-cellulose composite.

In some embodiments, the process further comprises recovering, combusting, or further treating the lignin that does not deposit onto the cellulose-rich solids during step (c). The process may further comprise chemically converting the lignin-coated cellulose material to one or more lignin-coated cellulose derivatives such as cellulose esters, cellulose ethers, cellulose ether esters, alkylated cellulose compounds, cross-linked cellulose compounds, acid-functionalized cellulose compounds, base-functionalized cellulose compounds, or combinations thereof.

The biomass feedstock may be selected from hardwoods, softwoods, forest residues, *eucalyptus*, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, *miscanthus*, energy cane straw/residue, or combinations thereof. The process disclosed herein benefits from feedstock flexibility; it is effective for a wide variety of cellulose-containing feedstocks.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.). Various moisture levels may be associated with the starting biomass. The biomass feedstock need not be, but may be, relatively dry. In general, the biomass is in the form of a particulate or chip, but particle size is not critical in this invention.

Some variations provide a process for producing a hydrophobic cellulose material, the process comprising:

(a) providing a lignocellulosic biomass feedstock;

(b) fractionating the feedstock in the presence of an acid, a solvent for lignin, and water, to generate cellulose-rich solids and a liquid containing hemicellulose and lignin, wherein a portion of the lignin deposits onto a surface of the cellulose-rich solids, thereby rendering the cellulose-rich solids at least partially hydrophobic;

(c) optionally mechanically treating the cellulose-rich solids to form cellulose fibrils and/or cellulose crystals, having a crystallinity of at least 60%; and (d) recovering the hydrophobic cellulose material.

In some embodiments, the acid is selected from the group consisting of sulfur dioxide, sulfurous acid, sulfur trioxide, sulfuric acid, lignosulfonic acid, and combinations thereof.

The crystallinity of the hydrophobic cellulose material may at least 70% or at least 80%. The hydrophobic cellulose material may be characterized by an average degree of polymerization from about 100 to about 1500, such as about 300 to about 700 or about 150 to about 250.

Optionally, the process further comprises chemically modifying the lignin to increase hydrophobicity of the hydrophobic cellulose material. Such modification to lignin could be done in solution or after the lignin is deposited onto cellulose.

Variations provide a process for producing a cellulose-containing product, the process comprising providing a lignin-coated cellulose material or a hydrophobic cellulose material, and then incorporating at least a portion of the lignin-coated cellulose material or the hydrophobic cellulose material into a cellulose-containing product.

In some embodiments, the process comprises forming a structural object that includes the cellulose material, or a derivative thereof. In certain embodiments, the process comprises forming a foam or aerogel that includes the cellulose material, or a derivative thereof.

In some embodiments, the process comprises combining the cellulose material, or a derivative thereof, with one or more other materials to form a composite. The one or more other materials may include a polymer selected from polyolefins, polyesters, polyurethanes, polyamides, or combinations thereof. The one or more other materials may include carbon.

In some embodiments, the process comprises forming a film (such as a flexible film) comprising the cellulose material, or a derivative thereof. In some embodiments, the process comprises forming a coating or coating precursor comprising the cellulose material, or a derivative thereof.

In some embodiments, the cellulose-containing product is configured electrochemically for carrying or storing an electrical current or voltage.

In some embodiments, the cellulose-containing product is incorporated into a filter, membrane, or other separation device.

In some embodiments, the cellulose-containing product is incorporated as an additive into a coating, paint, or adhesive.

In some embodiments, the cellulose-containing product is configured as a catalyst, catalyst substrate, or co-catalyst.

In some embodiments, the cellulose-containing product is incorporated as a cement additive.

In some embodiments, the cellulose-containing product is a paper coating.

In some embodiments, the cellulose-containing product is incorporated as a thickening agent or rheological modifier.

In some embodiments, the cellulose-containing product is incorporated as an additive in a drilling fluid, such as an oil recovery fluid and/or a gas recovery fluid.

A hydrophobic cellulose composition is disclosed with a cellulose crystallinity of about 70% or greater, wherein the hydrophobic cellulose composition contains cellulose particles having a surface concentration of lignin that is greater than a bulk concentration of lignin.

In some embodiments, the cellulose crystallinity is about 75% or greater, such as about 80% or 80% or greater.

In some embodiments, the hydrophobic cellulose composition further comprises sulfur. The sulfur may be derived from the process to produce the hydrophobic cellulose, or otherwise incorporated into the composition.

In some embodiments, the hydrophobic cellulose composition is characterized by an average cellulose degree of polymerization from about 100 to about 1500, such as about 300 to about 700 or about 150 to about 250. The composition may be characterized by a cellulose degree of polymerization distribution having a single peak or two peaks, for example.

In various embodiments, the cellulose-containing product is selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

In some embodiments, the cellulose-rich solids are treated with a total mechanical energy of less than about 1000 kilowatt-hours per ton of the cellulose-rich solids, such as less than about 950, 900, 850, 800, 750, 700, 650, 600, 550, 500, 450, 400, 350, 300, or 250 kilowatt-hours per ton of the cellulose-rich solids. In certain embodiments, the total mechanical energy is from about 100 kilowatt-hours to about 400 kilowatt-hours per ton of the cellulose-rich solids. Energy consumption may be measured in any other suitable units. An ammeter measuring current drawn by a motor driving the mechanical treatment device is one way to obtain an estimate of the total mechanical energy.

Mechanically treating (when conducted) may employ one or more known techniques such as, but by no means limited to, milling, grinding, beating, sonicating, or any other means to form or release fibrils and/or crystals in the cellulose. Essentially, any type of mill or device that physically separates fibers may be utilized. Such mills are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, Handbook for Pulp & Paper Technologists, Tappi Press, 1992.

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

Following mechanical treatment, the cellulose material may be classified by particle size. A portion of material may be subjected to a separate process, such as enzymatic hydrolysis to produce glucose. Such material may have good crystallinity, for example, but may not have desirable particle size or degree of polymerization.

Some embodiments may further comprise treatment of the cellulose-rich solids with one or more enzymes or with one or more acids. When acids are employed, they may be selected from the group consisting of sulfur dioxide, sulfurous acid, lignosulfonic acid, acetic acid, formic acid, and combinations thereof. Acids associated with hemicellulose, such as acetic acid or uronic acids, may be employed, alone or in conjunction with other acids. Also, the process may include treatment of the cellulose-rich solids with heat.

When an acid is employed, the acid may be a strong acid such as sulfuric acid, nitric acid, or phosphoric acid, for example. Weaker acids may be employed, under more severe temperature and/or time. Enzymes that hydrolyze cellulose (i.e., cellulases) and possibly hemicellulose (i.e., with hemicellulase activity) may be employed in step (c), either instead of acids, or potentially in a sequential configuration before or after acidic hydrolysis.

In some embodiments, the process comprises enzymatically treating the cellulose-rich solids to hydrolyze amorphous cellulose. In other embodiments, or sequentially prior to or after enzymatic treatment, the process may comprise acid-treating the cellulose-rich solids to hydrolyze amorphous cellulose.

In some embodiments, the process further comprises enzymatically treating the crystalline cellulose. In other embodiments, or sequentially prior to or after enzymatic treatment, the process further comprises acid-treating treating the crystalline cellulose.

If desired, an enzymatic treatment may be employed prior to, or possibly simultaneously with, mechanical treatment. However, in preferred embodiments, no enzyme treatment is necessary to hydrolyze amorphous cellulose or weaken the structure of the fiber walls before isolation of fibers.

In some embodiments, the crystallinity of the cellulose-rich solids is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86% or higher. In these or other embodiments, the crystallinity of the cellulose material is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86% or higher. The crystallinity may be measured using any known techniques. For example, X-ray diffraction and solid-state $^{13}C$ nuclear magnetic resonance may be utilized.

In some embodiments, the cellulose material is characterized by an average degree of polymerization from about 100 to about 1500, such as about 125, 150, 175, 200, 225, 250, 300, 400, 500, 600, 700, 800, 900, 1000, 1100, 1200, 1300, or 1400. For example, the cellulose material may be characterized by an average degree of polymerization from about 300 to about 700, or from about 150 to about 250. The cellulose material, when in the form of crystals, may have a degree of polymerization less than 100, such as about 75, 50, 25, or 10. Portions of the material may have a degree of polymerization that is higher than 1500, such as about 2000, 3000, 4000, or 5000.

In some embodiments, the cellulose material is characterized by a degree of polymerization distribution having a single peak. In other embodiments, the cellulose material is characterized by a degree of polymerization distribution having two peaks, such as one centered in the range of 150-250 and another peak centered in the range of 300-700.

In some embodiments, the cellulose material is characterized by an average length-to-width aspect ratio of particles from about 10 to about 1000, such as about 15, 20, 25, 35, 50, 75, 100, 150, 200, 250, 300, 400, or 500. Fibrils are generally associated with higher aspect ratios than crystals. Nanocrystals, for example, may have a length range of about 100 nm to 500 nm and a diameter of about 4 nm, translating to an aspect ratio of 25 to 125. Nanofibrils may have a length of about 2000 nm and diameter range of 5 to 50 nm, translating to an aspect ratio of 40 to 400. In some embodiments, the aspect ratio is less than 50, less than 45, less than 40, less than 35, less than 30, less than 25, less than 20, less than 15, or less than 10.

Optionally, the process further comprises hydrolyzing amorphous cellulose into glucose in, and fermenting the glucose to a fermentation product. Optionally, the process further comprises recovering, fermenting, or further treating hemicellulosic sugars derived from the hemicellulose. Optionally, the process further comprises recovering, combusting, or further treating the lignin (i.e., the lignin that did not deposit onto the cellulose).

Glucose that is generated from hydrolysis of amorphous cellulose may be integrated into an overall process to produce ethanol, or another fermentation co-product. Thus in some embodiments, the process further comprises hydrolyzing amorphous cellulose into glucose, and recovering the glucose. The glucose may be purified and sold. Or the glucose may be fermented to a fermentation product, such as but not limited to ethanol. The glucose or a fermentation product may be recycled to the front end, such as to hemicellulose sugar processing, if desired.

When hemicellulosic sugars are recovered and fermented, they may be fermented to produce a monomer or precursor thereof. The monomer may be polymerized to produce a polymer, which may then be combined with the cellulose material to form a polymer-cellulose composite.

In some embodiments, the process further comprises chemically converting the cellulose material to one or more cellulose derivatives. For example, cellulose derivatives may be selected from the group consisting of esters, ethers, ether esters, alkylated compounds, cross-linked compounds, acid-functionalized compounds, base-functionalized compounds, and combinations thereof.

Various types of cellulose functionalization or derivatization may be employed, such as functionalization using polymers, chemical surface modification, functionalization using nanoparticles, modification with inorganics or surfactants, or biochemical modification.

In some embodiments, the $SO_2$ concentration is from about 12 wt % to about 30 wt %. In some embodiments, the fractionation temperature is from about 140° C. to about 170° C. In some embodiments, the fractionation time is from about 1 hour to about 2 hours. The process is controlled such that a portion of the solubilized lignin (or another source of lignin) intentionally deposits back onto a surface of the cellulose-rich solids, thereby rendering the cellulose-rich solids at least partially hydrophobic.

A significant factor limiting the application of strength-enhancing, lightweight cellulose in composites is cellulose's inherent hydrophilicity. Surface modification of the cellulose surface to impart hydrophobicity to enable uniform dispersion in a hydrophobic polymer matrix is an active area of study. It has been discovered that when preparing cellulose using the processes described herein, lignin may condense on pulp under certain conditions, giving a rise in Kappa number and production of a brown or black material. The lignin increases the hydrophobicity of the cellulose precursor material, and that hydrophobicity is retained provided that there is not removal of the lignin through bleaching or other steps. (Some bleaching may still be performed, either to adjust lignin content or to attack a certain type of lignin, for example.)

Process conditions may be varied to accomplish the desire degree of lignin deposition. Conditions which tend to promote lignin deposition onto fibers are extended time and/or temperature, reduced pH, and reduced concentration of solvent for lignin (e.g., about 40 wt %, 35 wt %, 30 wt %, 25 wt %, 20 wt %, or less ethanol). Alternatively, or additionally, the process may include one or more washing steps that are adapted to deposit at least some of the lignin that was solubilized during the initial fractionation. One approach is to wash with water rather than a solution of water and solvent. Because lignin is generally not soluble in water, it will begin to precipitate. Optionally, other conditions may be varied, such as pH and temperature, during fractionation, washing, or other steps, to optimize the amount of lignin deposited on surfaces. It is noted that in order for the lignin surface concentration to be higher than the bulk concentration, the lignin needs to be first pulled into solution and then redeposited; internal lignin (within particles of cellulose) does not enhance hydrophobicity in the same way.

Optionally, the process for producing a hydrophobic cellulose material may further include chemically modifying the lignin to increase hydrophobicity of the cellulose material. The chemical modification of lignin may be conducted during fractionation, during deposition, following deposition, or some combination thereof.

High loading rates of lignin have been achieved in thermoplastics. Even higher loading levels are obtained with well-known modifications of lignin. The preparation of useful polymeric materials containing a substantial amount of lignin has been the subject of investigations for more than thirty years. Typically, lignin may be blended into polyolefins or polyesters by extrusion up to 25-40 wt % while satisfying mechanical characteristics. In order to increase the compatibility between lignin and other hydrophobic polymers, different approaches have been used. For example, chemical esterification of lignin may be accomplished through esterification with long-chain fatty acids.

Any known chemical modifications may be carried out on the lignin, to further increase the hydrophobic nature of the lignin-coated cellulose material provided by embodiments of this invention.

The cellulose material may further contain some sulfonated lignin that is derived from sulfonation reactions with $SO_2$ (when used as the acid in fractionation) during the biomass digestion. The amount of sulfonated lignin may be about 0.1 wt % (or less), 0.2 wt %, 0.5 wt %, 0.8 wt %, 1 wt %, or more. Also, without being limited by any theory, it is speculated that a small amount of sulfur may chemically react with cellulose itself, in some embodiments.

A cellulose-containing product may include any of the disclosed hydrophobic, lignin-coated cellulose compositions. Many cellulose-containing products are possible. For example, a cellulose-containing product may be selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

In some embodiments, the cellulose-containing product is a moisture-barrier pressed pulp product. In numerous applications including packaging, moisture may be present. In a moisture content situation, a moisture barrier is desirable to prevent, or at least slow, the leakage of any moisture. Currently, a pulp product may be treated to produce an end product having a moisture barrier. Conventional methods of creating moisture barrier products include coating linerboard with a polymeric water-repellant laminate, or coating linerboard with wax or a wax-like substance. However, each of these methods adds significant production costs to the fabrication process. Beyond production costs, these processes produce a resultant moisture barrier product that is not completely repulpable and, in fact, is often rejected by recycling plants only to end up in a landfill. Moreover, the resultant moisture barrier product has a surface coating that can affect production. For instance, the surface coating is often difficult to print on thereby requiring a special ink. The surface coating may also create problems in gluing portions of the corrugated to form a container, the glue not adhering well to the surface coating. The surface coating is easily scratched reducing the effectiveness of the moisture barrier protection.

In some embodiments of the invention, a moisture-barrier pulp product is provided by lignin-coated, hydrophobic material. The moisture-barrier pulp product may be incorporated into a variety of final products and geometries, including coatings, structural objects (e.g., containers), and so on. In some embodiments, the moisture-barrier pulp product is a moisture-barrier pressed pulp product. In some embodiments, the moisture-barrier pulp product is a moisture-barrier molded pulp product. In some embodiments, the moisture-barrier pulp product is a moisture-barrier extruded pulp product.

Figure 2:
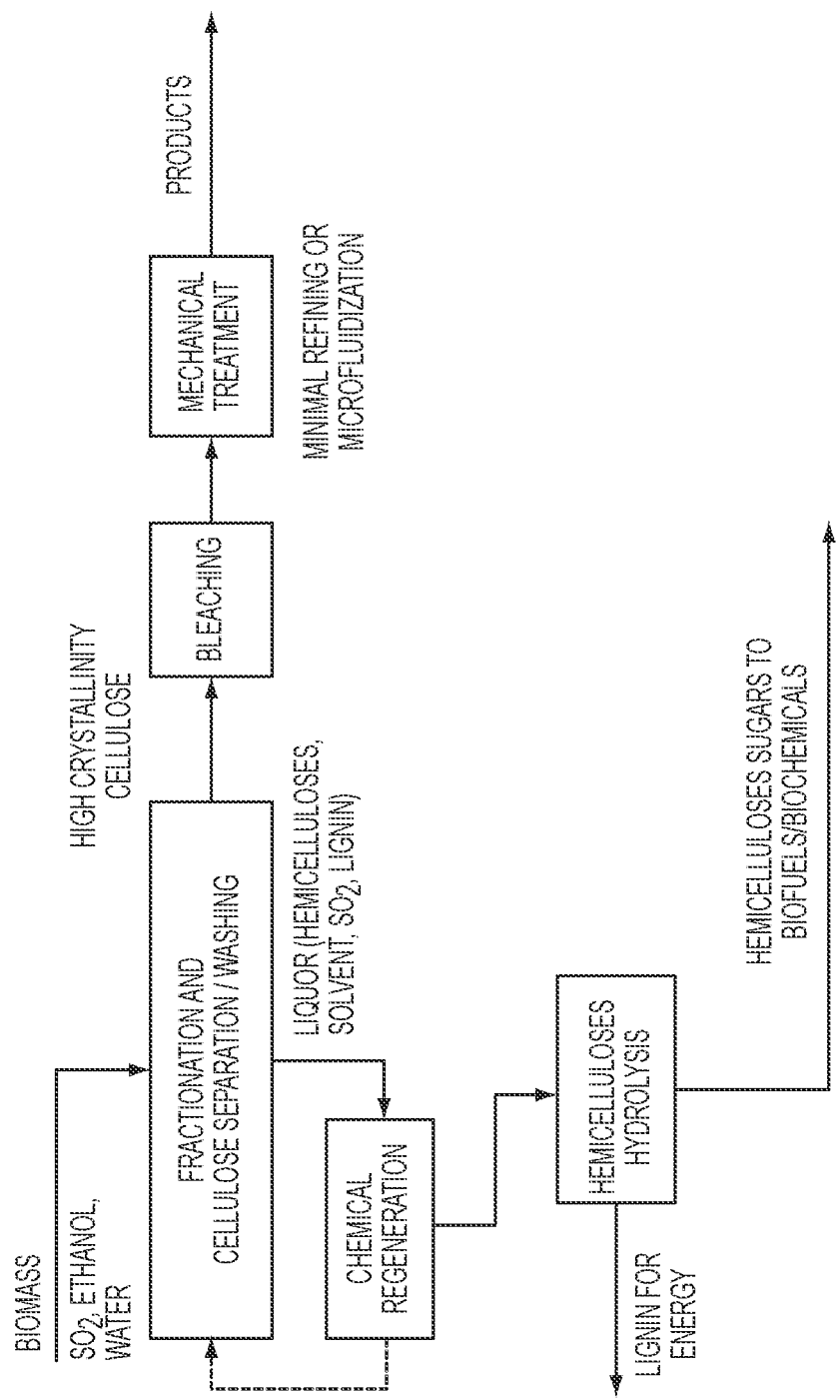
FIG. 2 depicts the production of lignin-coated cellulose materials from biomass, according to some embodiments of the invention. Mechanical treatment and bleaching are both optional.
Figure 3:
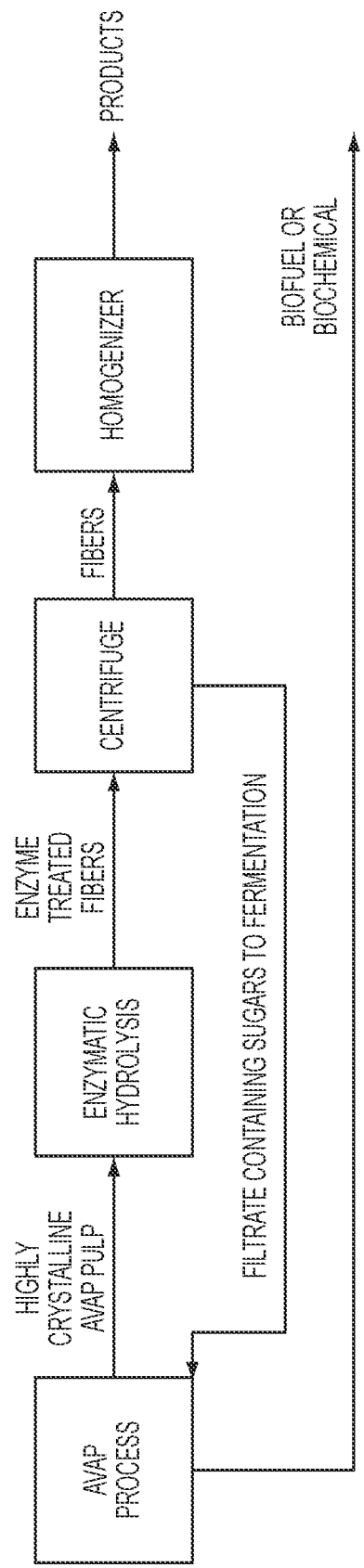
FIG. 3 depicts the production of lignin-coated cellulose materials from biomass, according to some embodiments of the invention.
Figure 4:
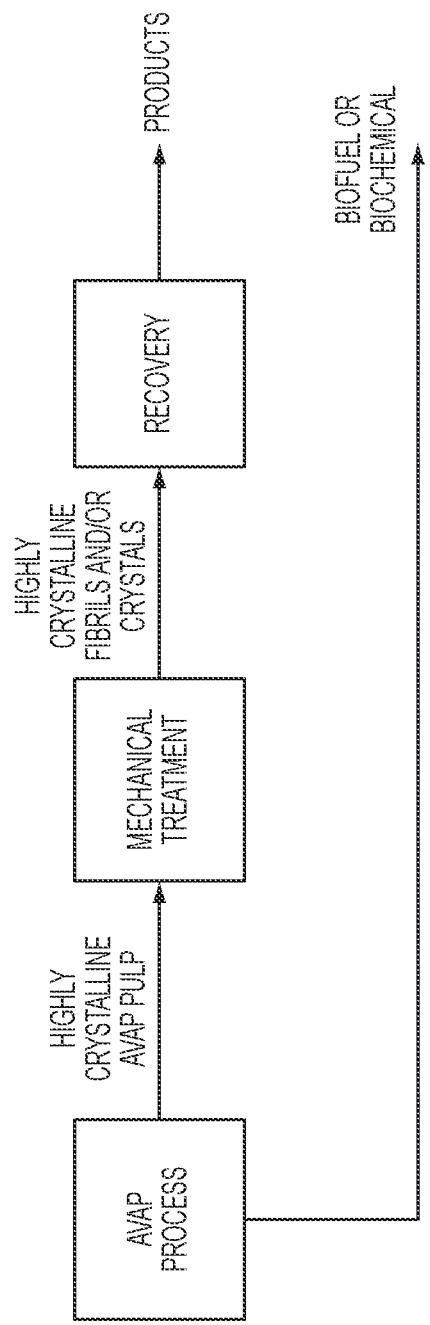
FIG. 4 depicts the production of lignin-coated cellulose materials from biomass, according to some embodiments of the invention. Mechanical treatment is optional.

Some process variations may be understood with reference to FIGS. 1-4. Dotted lines denote optional streams. Various embodiments will now be further described, without limitation as to the scope of the invention. These embodiments are exemplary in nature.

In some embodiments, a first process step is "cooking" (equivalently, "digesting") which fractionates the three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 3 wt %, preferably at least 6 wt %, more preferably at least 8 wt %, such as about 9 wt %, 10 wt %, 11 wt %, 12 wt %, 13 wt %, 14 wt %, 15 wt %, 20 wt %, 25 wt %, 30 wt % or higher. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 190° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfate ions, combinations thereof, or a salt of any of the foregoing. Excess sulfur dioxide, following hydrolysis, may be recovered and reused.

In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present both in the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize or enhance the reprecipitation of the extracted lignin on the solid phase. Minimizing lignin reprecipitation is favored by conducting separation or washing at a temperature of at least the glass-transition temperature of lignin (about 120° C.); conversely, enhancing lignin reprecipitation is favored by conducting separation or washing at a temperature less than the glass-transition temperature of lignin.

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digester, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about −0.1 atmospheres to about 10 atmospheres, such as about 0.1 atm, 0.3 atm, 0.5 atm, 1.0 atm, 1.5 atm, 2 atm, 4 atm, 6 atm, or 8 atm.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10% (e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as Clostridia bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO_4 \cdot 7H_2O$, that oxidizes sulfite ions to sulfate ions. Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

The process lignin separation step is for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

The present invention also provides systems configured for carrying out the disclosed processes, and compositions produced therefrom. Any stream generated by the disclosed processes may be partially or completed recovered, purified or further treated, and/or marketed or sold.

Certain cellulose-containing products provide high transparency, good mechanical strength, and/or enhanced gas (e.g., $O_2$ or $CO_2$) barrier properties, for example. Certain cellulose-containing products containing hydrophobic cellulose materials provided herein may be useful as anti-wetting and anti-icing coatings, for example.

Some embodiments provide cellulose-containing products with applications for sensors, catalysts, antimicrobial materials, current carrying and energy storage capabilities. Cellulose crystals have the capacity to assist in the synthesis of metallic and semiconducting nanoparticle chains.

Some embodiments provide composites containing cellulose and a carbon-containing material, such as (but not limited to) lignin, graphite, graphene, or carbon aerogels.

Cellulose may be coupled with the stabilizing properties of surfactants and exploited for the fabrication of nanoarchitectures of various semiconducting materials.

The reactive surface of —OH side groups in cellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other cellulose applications suitable to the present invention include reinforced polymers, high-strength spun fibers and textiles, advanced composite materials, films for barrier and other properties, additives for coatings, paints, lacquers and adhesives, switchable optical devices, pharmaceuticals and drug delivery systems, bone replacement and tooth repair, improved paper, packaging and building products, additives for foods and cosmetics, catalysts, and hydrogels.

Aerospace and transportation composites may benefit from high crystallinity. Automotive applications include cellulose composites with polypropylene, polyamide (e.g. Nylons), or polyesters (e.g. PBT).

Cellulose materials provided herein are suitable as strength-enhancing additives for renewable and biodegradable composites. The cellulosic fibrillar structures may function as a binder between two organic phases for improved fracture toughness and prevention of crack formation for application in packaging, construction materials, appliances, and renewable fibers.

Cellulose materials provided herein are suitable as transparent and dimensional stable strength-enhancing additives and substrates for application in flexible displays, flexible circuits, printable electronics, and flexible solar panels. Cellulose is incorporated into the substrate-sheets are formed by vacuum filtration, dried under pressure and calandered, for example. In a sheet structure, cellulose acts as a glue between the filler aggregates. The formed calandered sheets are smooth and flexible.

Cellulose materials provided herein are suitable for composite and cement additives allowing for crack reduction and increased toughness and strength. Foamed, cellular cellulose-concrete hybrid materials allow for lightweight structures with increased crack reduction and strength.

Strength enhancement with cellulose increases both the binding area and binding strength for application in high strength, high bulk, high filler content paper and board with enhanced moisture and oxygen barrier properties.

Fibrillated cellulose nanopaper has a higher density and higher tensile mechanical properties than conventional paper. It can also be optically transparent and flexible, with low thermal expansion and excellent oxygen barrier characteristics. The functionality of the nanopaper can be further broadened by incorporating other entities such as carbon nanotubes, nanoclay or a conductive polymer coating.

Porous cellulose may be used for cellular bioplastics, insulation and plastics and bioactive membranes and filters. Highly porous cellulose materials are generally of high interest in the manufacturing of filtration media as well as for biomedical applications, e.g., in dialysis membranes.

Cellulose materials provided herein are suitable as coating materials as they are expected to have a high oxygen barrier and affinity to wood fibers for application in food packaging and printing papers.

Cellulose materials provided herein are suitable as additives to improve the durability of paint, protecting paints and varnishes from attrition caused by UV radiation.

Cellulose materials provided herein are suitable as thickening agents in food and cosmetics products. Cellulose can be used as thixotropic, biodegradable, dimensionally stable thickener (stable against temperature and salt addition). Cellulose materials provided herein are suitable as a Pickering stabilizer for emulsions and particle stabilized foam.

The large surface area of these cellulose materials in combination with their biodegradability makes them attractive materials for highly porous, mechanically stable aerogels. Cellulose aerogels display a porosity of 95% or higher, and they are ductile and flexible.

Drilling fluids are fluids used in drilling in the natural gas and oil industries, as well as other industries that use large drilling equipment. The drilling fluids are used to lubricate, provide hydrostatic pressure, and to keep the drill cool, and the hole as clean as possible of drill cuttings. Cellulose materials provided herein are suitable as additives to these drilling fluids.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing a lignin-coated cellulose material, said process comprising:
 (a) providing a lignocellulosic biomass feedstock;
 (b) fractionating said feedstock in the presence of an acid, a solvent for lignin, and water, to generate cellulose-rich solids and a liquid containing hemicellulose and lignin, wherein said feedstock, said acid, said solvent for lignin, and said water are all contained together in a digestor;

(c) depositing at least some of said lignin, from said liquid, onto a surface of said cellulose-rich solids to generate a lignin-coated cellulose material containing cellulose particles having a surface concentration of lignin that is greater than a bulk concentration of lignin;

(d) mechanically treating said lignin-coated cellulose material, wherein said mechanically treating releases cellulose fibrils and/or cellulose crystals; and (e) recovering said lignin-coated cellulose material, wherein cellulose crystallinity of said lignin-coated cellulose material is at least 60%, wherein said lignin-coated cellulose material is at least partially hydrophobic, and wherein said lignin-coated cellulose material is lignin-coated microfibrillated cellulose or lignin-coated microcrystalline cellulose.

2. The process of claim 1, wherein said acid is selected from the group consisting of sulfur dioxide, sulfurous acid, sulfur trioxide, sulfuric acid, lignosulfonic acid, and combinations thereof.

3. The process of claim 2, wherein said acid is sulfur dioxide.

4. The process of claim 3, wherein sulfur dioxide concentration in step (b) is from about 12 wt % to about 30 wt %.

5. The process of claim 1, wherein fractionation temperature in step (b) is from about 140° C. to about 170° C.

6. The process of claim 1, wherein fractionation time in step (b) is from about 1 hour to about 2 hours.

7. The process of claim 1, wherein steps (c) and (d) are integrated.

8. The process of claim 1, wherein said process further comprises treatment of said lignin-coated cellulose material with one or more enzymes.

9. The process of claim 1, wherein said process further comprises treatment of said lignin-coated cellulose material with one or more acids.

10. The process of claim 9, wherein said one or more acids are selected from the group consisting of sulfur dioxide, sulfurous acid, lignosulfonic acid, acetic acid, formic acid, and combinations thereof.

11. The process of claim 1, wherein said process further comprises treatment of said lignin-coated cellulose material with heat.

12. The process of claim 1, wherein said cellulose crystallinity of said lignin-coated cellulose material is at least 70%.

13. The process of claim 12, wherein said cellulose crystallinity of said lignin-coated cellulose material is at least 80%.

14. The process of claim 1, said process further comprising chemically converting said lignin-coated cellulose material to one or more lignin-coated cellulose derivatives.

15. The process of claim 14, wherein said lignin-coated cellulose derivatives are selected from the group consisting of cellulose esters, cellulose ethers, cellulose ether esters, alkylated cellulose compounds, cross-linked cellulose compounds, acid-functionalized cellulose compounds, base-functionalized cellulose compounds, and combinations thereof.

* * * * *